United States Patent [19]

Felder et al.

[11] 4,139,605

[45] Feb. 13, 1979

[54] WATER-SOLUBLE, NON-IONIZING, RADIOPAQUE COMPOUNDS AND CONTRAST COMPOSITIONS CONTAINING THE SAME

[75] Inventors: Ernst Felder, Riva San Vitale, Switzerland; Davide Pitré, Milan, Italy

[73] Assignee: Bracco Industria Chimica S.p.A., Milan, Italy

[21] Appl. No.: 881,567

[22] Filed: Feb. 27, 1978

[30] Foreign Application Priority Data

Mar. 28, 1977 [CH] Switzerland ............... 3806/77

[51] Int. Cl.² ............ A61K 29/02; C07C 103/24; C07C 103/26; C07C 103/28
[52] U.S. Cl. ............................ 424/5; 260/558 A; 260/558 D; 260/558 P; 260/559 A; 424/1.5; 424/324
[58] Field of Search ......... 424/5, 324; 260/558 A, 260/558 D, 558 P, 559 A

[56] References Cited

U.S. PATENT DOCUMENTS

| | | | |
|---|---|---|---|
| 3,660,469 | 5/1972 | Bernstein et al. | 424/5 X |
| 3,953,501 | 4/1976 | Klieger et al. | 260/558 A |
| 4,001,323 | 1/1977 | Felder et al. | 260/558 D |
| 4,005,188 | 1/1977 | Tilly et al. | 424/5 |
| 4,014,986 | 3/1977 | Tilly et al. | 424/5 |
| 4,032,567 | 6/1977 | Klieger et al. | 260/558 A |
| 4,062,934 | 12/1977 | Tilly et al. | 425/5 |

FOREIGN PATENT DOCUMENTS 855739 11/1970 Canada .................. 424/5

Primary Examiner—Albert T. Meyers
Assistant Examiner—Vera C. Clarke

Attorney, Agent, or Firm—Hans Berman

[57] ABSTRACT

α, ω-bis-[5-(dihydroxyalkyl) aminocarbonyl-3-hydroxyacyl-amino-2,4,6-triiodo-benzoyl-amino]-oxaalkane compounds of the formula

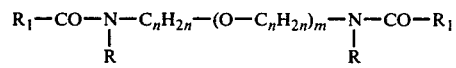

wherein
$R_1$ is

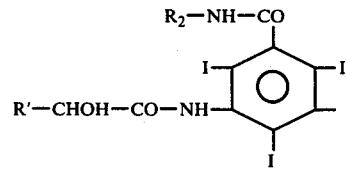

R and R' are hydrogen or methyl,
$R_2$ is dihydroxyalkyl having 3 or 4 carbon atoms,
n is 2 or 3,
m is an integer between 1 and 5, and
$n(m+1)$ is an integer between 4 and 12, are readily soluble in water to yield injectable radiopaque contrast compositions which are well tolerated and stable. The compounds are prepared in good yields by reacting a reactive derivative of a 5-(di-hydroxyalkyl)aminocarbonyl-3-acyloxyacylamino-2,4,6-triiodo-benzoic acid with an α,ω-diamino-oxaalkane of the formula

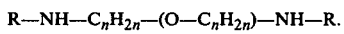

11 Claims, No Drawings

WATER-SOLUBLE, NON-IONIZING, RADIOPAQUE COMPOUNDS AND CONTRAST COMPOSITIONS CONTAINING THE SAME

The invention relates to radiography, and particularly to novel compounds having a high iodine content, to contrast compositions opaque to X-rays due to their content of the compounds, and to methods of producing the compounds.

In its more specific aspects, the invention is concerned with radiopaque compounds which are readily soluble in water without ionizing, and whose aqueous solutions have a low osmotic pressure. Such compounds, when not toxic, may be injected into blood vessels and other cavities of the human body, including cavities of the spinal cord and other parts of the central nervous system and the brain, in aqueous, concentrated solutions at relatively high rates without causing side effects in most patients. The known non-ionizing contrast agents are superior in this respect to radiopaque substances which are ionizing salts, but undesirable side effects still are observed, particularly in debilitated patients.

The primary object of this invention is the provision of compounds high in iodine content which are readily soluble in water, and whose concentrated, aqueous solutions have lower osmotic pressure than the solutions of the best compounds now in clinical use. A concomitant object is the provision of a method of making the compounds.

The compounds of the invention are α,ω-bis-[5-(dihydroxyalkyl)-aminocarbonyl-3-hydroxyacyl-amino-2,4,6-triiodo-benzoyl-amino]-oxaalkane compounds of the formula

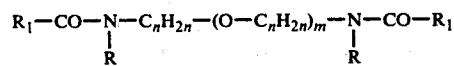

wherein
R₁ is

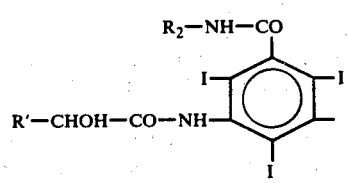

R and R' are hydrogen or methyl,
$R_2$ is dihydroxyalkyl having 3 or 4 carbon atoms,
n is 2 or 3,
m is an integer between 1 and 5, and
n(m+1) is an integer between 4 and 12.

In combination with a physiologically tolerated aqueous carrier, an effective amount of a compound of the invention constitutes an injectable contrast composition.

The compounds of the invention are prepared by reacting a reactive anydride of the formula which comprises reacting a reactive anhydride of the formula

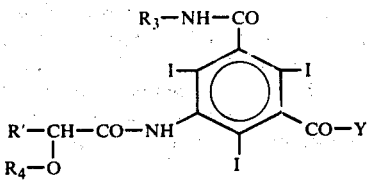

with an α,ω-diaminooxaalkane of the formula

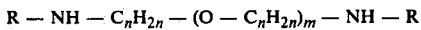

wherein
$R_3$ is $R_2$ or a ketal of said $R_2$,
$R_4$ is lower alkanoyl, and
CO — Y is the active radical of a mixed acid anhydride until each NH group in the α,ω-diaminooxaalkane reacts with the CO — Y group of the anhydride to form a CO — N bond, and thereafter splitting the ketal if $R_3$ is a ketal of $R_2$, and hydrolyzing the $R_4$ — O group.

Suitable representatives of Y are the acid radicals of acids, particularly of the hydrogen halides, hydrogen azide, phosphoric acid and its derivatives, carbonic acid and its derivatives, also acyloxy and alkoxycarbonyloxy radicals. The preferred representative of Y is chlorine.

When $R_3$ is a ketal of $R_2$, the hydroxyl groups of $R_2$ may be converted to radicals such as
4,4-dimethyl-3,5-dioxacyclohexyl,
3,3-dimethyl-2,4-dioxacyclopentyl-(1)-methyl,
3,5-dioxacyclohexyl,
4,4-diethyl-3,5-dioxacyclohexyl,
4-methyl-4-ethyl-2,5-dioxacyclohexyl.

The ketal forming group is quickly and conveniently removed when its protective function for the hydroxyl groups is no longer required, as by a brief treatment with a strong acid, such as very dilute hydrochloric acid or a strongly acidic ion exchange resin, whereby the corresponding oxo-compound, such as acetone, is set free.

The lower alkanoyl group $R_4$, such as acetyl, propionyl, or butyryl is readily hydrolyzed by treatment with aqueous alkali metal hydroxide solutions.

The reaction between the reactive anhydride and the α,ω-diamino-oxaalkane is preferably carried out in an aprotic solvent, such as dimethylacetamide, dimethylformamide, hexamethylphosphoric acid triamide, dioxane, acetone, and the like. The reaction temperature is not critical, and the reaction is preferably performed in the approximate temperature range between −10° C. and +150° C.

The iodine atoms in the compounds of the invention may be replaced by radioactive iodine in a known manner, or the compounds may be prepared from reactants labeled with radioactive iodine. The radioactive compounds are useful for scintigraphy and for special diagnostic purpose.

The compounds of the invention compare favorably in their low toxicity with the best non-ionic contrast agents now in clinical use, and their concentrated aqueous solutions have osmotic pressures significantly lower than those of the known agents. The specific structure of the molecules in the compounds of the invention is thought to account for the observed low pressure.

Properties of compounds A, B, C, D of this invention, of the chemically nearest known compounds E, F, and of chemically less closely related known radiopaque compounds G, H, I used heretofore for visualizing blood vessels and cavities of the spinal cord and the brain are listed in the Table hereinbelow. Toxicity is listed as $LD_{50}$ in mg I/kg body weight 12 days after intravenous injection and 48 hours after intracerebral injection in mice. The osmotic pressure was determined at 37° C. in solutions containing 400 mg I per ml, unless specifically noted otherwise, and is indicated in atmospheres.

Compounds of the invention and known compounds are identified in the Table by capital letters as follows:

A: 1,8-bis-[5,-(1,3-dihydroxyisopropyl) aminocarbonyl-3-(2-hydroxypropionyl) amino-2,4,6-triiodo-benzoylamino]-3,6,dioxaoctane B: 1,16-bis-[5-(1,3-dihydroxyisopropyl) aminocarbonyl-3-(2-hydroxypropionyl) amino-2,4,6-triiodobenzoylamino]-4,7,10,13-tetraoxahexadecane C: 1,11-bis [N-methyl-N-{5-(1,3-dihydroxyisopropyl-)aminocarbonyl-3-(2-hydroxypropionyl) amino-2,4,6-triiodobenzoyl}-amino]-3,6,9-trioxaundecane D: 1,16-bis-[N-methyl-N-{5-(1,3-dihydroxyisopropyl-)aminocarbonyl-3-(2-hydroxypropionyl) amino-2,4,6-triiodobenzoyl}amino]-4,7,10,13-tetraoxahexadecane E: 5-α-hydroxypropionylamino-2,4,6-triiodo-isophthalic acid-bis-(1,3-dihydroxyisopropylamide) (U.S. Pat. No. 4,001,323)

F: 3-acetylamino-5-N-methyl-acetylamino-2,4,6-triiodo-benzoyl-glucosamine (metrizamide)

G: 5,5'-adipoyldiimino-bis-(2,4,6-triiodo-N-methyl-isophthalamic acid) (iocarmic acid)

H: 5,5',5''-(nitrilotriacetyl-triimino-tris-)-2,4,6-triiodo-N'-methyl-isophthalamic acid (German Patent Publication No. 2,132,614)

I: 3,5-bis-acetylamino-2,4,6-triiodobenzoic acid (amidotriozate)

Table

| Compound | Toxicity, mg I/kg mouse | | Osmotic pressure, atm. |
|---|---|---|---|
| | intravenous | intracerebral | |
| A | | 1100 | 8.15 |
| B | | 990 | |
| C | 14000 | 1130 | 10.59 |
| D | | 1420 | 9.42 |
| E | 21800 | 1500 | 22.2 |
| F | 10200 | 1400 | 14.7 |
| G | 5500 | 600 | 27.5[1] |
| H | 5800 | | 36.2 |
| I | 7600 | 55 | 51[2] |

[1]280 mg I/ml
[2]370 mg I/ml

The α,ω-bis-[5-(dihydroxyalkyl) aminocarbonyl-3-hydroxy-acylamino-2,4,6-triiodobenzoyl-amino]-oxoalkane compounds of the invention find their most useful application in the form of contrast compositions in which they are dissolved in a physiologically tolerated aqueous carrier liquid in concentrations that may typically range from 15 to more than 70% by weight so that the compositions contain from approximately 60 to approximately 500 mg iodine per milliliter. Solutions containing approximately 400 mg per ml are most widely applicable and therefore preferred. The specific mode of application will be readily chosen by those skilled in the art to suit specific requirements.

For myelography and radiculography, the solutions are instilled after lumbar or suboccipital puncture. For ventriculography, the ventricles are directly injected. The average dosage rate of the contrast compositions containing 400 mg I per ml is approximately 5 to 15 ml for myelography, 3 to 5 ml for radiculography, about 1 to 2 ml for ventriculography.

The aqueous solutions of the compounds of the invention show low toxicity to the central nervous system and are well tolerated even when injected into the spinal cord. Repeated lumbar injections into the subarachnoid space did not cause a rise in the body temperature of the patient and produced excellent contrast in pictures of the spinal canal, thereby permitting clear visualization of stenoses in the spinal canal.

When the contrast compositions of the invention are injected into lymph vessels, the vessels as well as the lymph nodes became clearly visible in radiographs. The contrast vanishes within a few hours because the iodine-bearing compounds of the invention are quickly excreted without change in chemical structure.

The preferred compounds of the invention are those identified in the table above by letters B and C. They combine solubility in water and lack of side effects in a particularly favorable manner. Their aqueous solutions containing more than 400 ml I per ml have relatively low viscosity at body temperature so that they are well suited for injection. The solutions are stable and have a long storage life. The intracisternal toxicity of Compound C is particularly low. $LD_{50}$ (48 hours) in rabbits is about 233 mg I per kg.

The following Examples are illustrative of the methods of making the compounds of the invention and of the formulation of injectable compositions containing the same.

EXAMPLE 1

99.2 g (0.14 mole) 5-(2-acetoxypropionyl)amino-2,4,6-triiodo-isophthalyl dichloride, prepared by the method of German Pat. No. 2,547,789, and 27.50 g (0.28 mole) 1,3-dihydroxy-isopropylamine were mixed with 500 ml dioxane, and the mixture was agitated at 60° C. for a few hours and filtered hot. 5-1,3-Dihydroxyisopropyl) aminocarbonyl-3-(2-acetoxypropionyl)amino-2,4,6-triiodobenzoyl chloride crystallized from the filtrate in an amount of 80 g (70% yield) and melted at 280° C. (decomp.).

44 g (0.06 mole) of the acyl chloride so prepared was dissolved in 200 ml dimethyl-acetamide and 13 g (0.07 mole) tributylamine was added. The mixture was stirred and cooled with water and ice while a solution of 4.9 g (0.033 mole) 1,8-diamino-3,6-dioxaoctane (Dietrich et al., Tetrahedron 1973, 1629) in the same solvent was added dropwise over approximately one hour. Stirring was continued at room temperature for several hours, whereupon the solvent was removed by evaporation in a vacuum. The residue was suspended in methylene chloride, the suspension was filtered, and the solids retained on the filter were dissolved in water. The aqueous solution was stripped of residual organic solvents in a vaccum, adjusted to pH 11 by adding 2N sodium hydroxide solution, and the addition of sodium hydroxide was continued until the pH value no longer drifted, that is, the acetoxy groups had been removed by saponification.

Salts were removed from the solution by passing the same sequentially over columns of cation exchange resin and anion exchange resin, and further purified by treatment with active char. It was then evaporated to dryness and the solid residue was recrystallized from ethanol.

Compound A was recovered in an amount of 30 g (65% yield), melted at 230°–235° C., and contained 49.85% iodine (50.09% calculated for $C_{34}H_{42}I_6N_6O_{14}$). An $R_f$ value of 0.57 was determined in a thin layer chromatogram on silica gel with MEK/glacial acetic acid/water 15:3:5.

The compound is soluble in water to form solutions of about 50 g/100 ml at 20° C., 100 g/100 ml at boiling temperature. It is also soluble in methanol, and sparingly soluble in ethanol (about 1% at room temperature, about 2.5% in boiling ethanol).

EXAMPLE 2

49.63 g (0.07 mole) 5-(2-acetoxypropionyl)amino-2,4,6-triiodoisophthalyl dichloride and 18.34 g (0.14 mole) 5-amino-2,2-di-methyl-1,3-dioxane (Swiss Pat. No. 550,003) were stirred in 300 ml dioxane at 40°–60° C. for one hour, and thereafter for about 2 hours at 80°–90° C., and the reaction mixture was filtered hot. 49 g 5-(4,4-Dimethyl-3,5-dioxacyclohexyl) aminocarbonyl-3-(2-acetoxypropionyl) amino-2-4-6-triiodobenzoyl chloride crystallized from the filtrate. It melted at about 300° C. (decomp.).

The compound was reacted with 1,8-diamino-3,6-dioxaoctane in the manner described in Example 1. The resulting 1,8-bis-[5-(4,4-dimethyl-3,5-dioxacyclohexyl) aminocarbonyl-3-(2-acetoxypropionyl) amino-2,4,6-triiodobenzoyl) amino]-3,6-dioxaoctane was dissolved in a small amount of 0.1 N hydrochloric acid, whereby acetone was split off from the 4,4-dimethyl-3,5-dioxacyclohexyl-amino radical. The solution of 1,8-bis-[5-(1,3-dihydroxy-isopropyl) aminocarbonyl-3-(2-acetoxypropionyl) amino-2,4,6-triiodobenzoyl-amino]-3,6-dioxaoctane was adjusted to pH 11 with 2N sodium hydroxide solution, and more sodium hydroxide was added until saponification of the acetoxy groups was complete.

The solution was further worked up as described in Example 1 to yield Compound A having a melting point of 233°–236° C.

EXAMPLE 3

53.4 g (0.07 mole) 5-(1,3-dihydroxyisopropyl)aminocarbonyl-3-(2-acetoxypropionyl) amino-2,4,6-triiodobenzoyl chloride was reacted with 7.5 g (0.039 mole) 1,11-diamino-3,6,9-trioxaundecane (Dietrich et al., l.c.) in 250 ml dimethylacetamide in the presence of 14.8 g (0.08 mole) tributylamine in the manner of Example 1. 1,11-Bis-[5-(1,3-dihydroxyisopropyl) aminocarbonyl-3-(2-hydroxy-propionyl) amino-2,4,6-triiodo-benzoylamino]-3,6,9-trioxaundecane was recovered in an amount of 40 g (74% yield) and melted at 220° C. It contained 48.29% iodine (48.67% calculated for $C_{36}H_{46}I_6N_6O_{15}$). An $R_f$ value of 0.53 was found in a thin layer chromatogram with the solvent system of Example 1.

EXAMPLE 4

45.9 g (0.06 mole) 5-(1,3-dihydroxyisopropyl)-aminocarbonyl-3-(2-acetoxypropionyl) amino-2,4,6-triiodo-benzoyl chloride was reacted with 8.75 g 1,16-diamino-4,7,10,13-tetraoxahexadecane in 200 ml dimethylacetamide in the presence of 13 g tributylamine as in Example 1, and the reaction mixture was worked up as described there.

Compound B was recovered in an amount of 38 g (77.6% yield) and melted at 197°–200° C. It contained 46.40% iodine (46.53% calculated for $C_{40}H_{54}I_6N_6O_{16}$). The thin layer chromatogram gave an $R_f$ value of 0.42 with chloroform/methanol/25% ammonium hydroxide solution 6:3:1. The compound dissolves in water at 20° C. at a rate of approximately 100 g/100 ml solution. It dissolves in boiling methanol at 50 g/100 ml.

EXAMPLE 5

40 g 5-(1,3-Dihydroxyisopropyl)-aminocarbonyl-3-(2-hydroxy-propionyl) amino-2,4,6-triiodo-benzoyl chloride and 6.4 g 1,11-bis-(N-methyl-amino)-3,6,9-trioxaundecane were reacted in 125 ml dimethylacetamide in the presence of 11.1 g tributylamine as in Example 1, and in the reaction mixture was worked up in the same manner to recover 17.3 g Compound C (37.5% yield) which decomposed at 215°–220° C. It contained 28.59% C, 47.6% I (28.67% C, 47.28% I calculated for $C_{38}H_{50}I_6N_6O_{15}$).

An $R_f$ value of 0.29 was established with the solvent system of Example 4. The compound dissolves readily in water, only moderately well in ethanol.

The 1,11-bis-(N-methylamino)-3,6,9-trioxaundecane was obtained by analogy with known procedures by refluxing 124 g (0.5 mole) 3,6,9-trioxaundecane-1,11-dioyl-bis-(N-methylamide) in 1500 ml tetrahydrofurane with 76 g (2 moles) lithium aluminum hydride. The desired product was obtained in an amount of 96 g (87% yield) and boiled at 164°–166° C. and 14 mm Hg.

EXAMPLE 6

1,16-Bis-(N-methylamino)-4,7,10,13-tetraoxahexadecane was prepared by suspending 120 g 1,16-bis (4-toluenesulfonyloxy)-4,7,10,13-tetraoxahexadecane in 180 ml 40% methylamine solution. The temperature of the suspension rose spontaneously, and the dispersed phase dissolved. The solution was saturated with solid sodium hydroxide, whereby sodium 4-toluenesulfonate was precipitated and could be removed by filtering. The filtrate was extracted with ethyl ether, and the extract was dried and evaporated to remove the solvent, whereby the desired compound was obtained. It boiled at 151° C. at 0.05 mm Hg.

45.9 g (0.06 Mole) 5-(1,3-dihydroxyisopropyl)aminocarbonyl-3-(2-acetoxypropionyl) amino-2,4,6-triiodo-benzoyl chloride was dissolved in 200 ml dimethylacetamide, and 13 g (0.07 mole) tributylamine was added. The mixture was stirred and cooled with water and ice while 9.6 g (0.033 mole) 1,16-bis-(N-methylamino)-4,7,10,13-tetraoxahexadecane diluted with 70 ml dimethylacetamide was added dropwise. Stirring was continued thereafter at room temperature for about four hours, and the reaction mixture was then left to stand overnight. It was thereafter evaporated in a vacuum, and the residue was dissolved in water and saponified by addition of sodium hydroxide as described above. Inorganic ions were removed by passage over a cation exchange resin and thereafter over an anion exchange resin, and the purified solution was evaporated to dryness. The residue was further dried and taken up in 600 ml boiling ethyl acetate. Compound D crystallized from the solvent in an amount of 36 g (72% yield).

It melted at 143°–168° C. and contained 45.25% iodine (45.74 calculated for $C_{42}H_{58}I_6N_6O_{16}$) and gave and $R_f$ value of 0.585 with the solvent system of Example 4. It dissolves very readily in water, and is soluble in methanol.

EXAMPLE 7

49.63 g 5-(2-acetoxypropionyl) amino-2,4,6-triiodoisophthalyl dichloride was reacted with 13.75 g 2,3-dihydroxypropylamine as in Example 2 to produce 5-(2,3-dihydroxypropyl) aminocarbonyl-3-(2acetoxypropionyl) amino-2,4,6-triiodo-benzoyl chloride. It melted at about 290° C. (decomp.).

49.9 g (0.05 mole) of the above acyl chloride was reacted with 9.6 g 1,16-bis(N-methylamino)-4,7,10,13-tetraoxahexadecane in 200 ml dimethylacetamide in the presence of 13 g tributylamine in the manner of Example 6. When the reaction mixture was worked up as described there, 30 g Compound D (60% yield) was obtained and melted at about 210° C (decomp.). It contained 45.51% iodine and readily dissolved in water.

EXAMPLE 8

5-(3,3-Dimethyl-2,4-dioxacyclopentyl-(1)-methyl) aminocarbonyl-3-(2-acetoxypropionyl) amino-2,4,6-triiodo-benzoyl chloride was prepared by the method of Example 2 from 49.63 g 5-(2-acetoxy-propionyl)amino-2,4,6-triiodoisophthalyl dichloride and 18.4 g 4-aminomethyl-2,2-dimethyl-1,3-dioxolane and melted at about 300° C. (decomp.).

It was reacted with 1,16-bis-(N-methylamino)-4,7,10,13-tetraoxahexadecane, and the resulting 1,16-bis-[N-methyl-N-{5-(3,3-dimethyl-2,4-dioxacyclopentyl-(1)-methyl) aminocarbonyl-3-(2-actoxypropionyl) amino-2,4,6-triiodobenzoyl}-amino]-4,7,10,13-tetraoxahexadecane was saponified by treatment with a little 0.1 N hydrochloric acid to product Compound D.

EXAMPLE 9

5-(1,3-dihydroxy-2-methyl-2-propyl) aminocarbonyl-3-(2-acetroxypropionyl) amino-2,4,6-triiodo-benzoyl choride was prepared in the manner of Example 2, by reacting 49.63 g (0.7 mole) 5-(2-acetoxypropionyl-)amino-2,4,6-triiodo-isophthalyl dichloride with 14.7 g (0.14 mole) 2-amino-2methyl-1,3-propanediol and melted at about 280° C. (decomp.).

46.75 g (0.06 mole) of the produce was reacted with 8.75 g 1,16-diamino-4,7,10,13-tetraoxahexadecane in 200 ml dimethylacetamide in the presence of 13 g tributylamine by the method of Example 1. The reaction mixture was worked up to isolate 36 g 1,16-bis-[5-(1,3-dihydroxy-2-methyl-2propyl) aminocarbonyl-3-(2-hydroxypropionyl) amino-2,4,6-triiodo-benzoylamino]-4,7,10,13tetraoxahexadecane.

The compound melted at approximately 220° C. (decomp.) and contained 45.29% iodine (45.74% calculated for $C_{42}H_{58}I_6N_6O_{16}$). It dissolves readily in water.

EXAMPLE 10

25.4 g (0.0326 Mole) 5-(1,3-dihydroxy-2-methyl-2propyl) aminocarbonyl-3-(2-acetoxypropionyl)amino-2,4,6-triiodo-benzoyl chloride was reacted with 3.65 g 1,14-diamino-3,6,9,12-tetraoxatetradecane (0.0154 mole) in 150 ml dimethylacetamide in the presence of 6.1 g tributylamine (0.033 mole) as in Example 1. 20.3 g 1,14-bis-[5-(1,3-dihydroxy-2methyl-2-propyl) aminocarbonyl-3-(2-hydroxypropionyl) amino-2,4,6-triiodo-benzoylamino]-3,6,9,12-tetraoxatetradecane was recovered (80.6% yield). The amorphous product softened at 80°-90° C. and gave an $R_f$ value of 0.41 with the solvent system of Example 1. It dissolved readily in water.

EXAMPLE 11

24.5 g 5-(1,3-dihydroxy-2methyl-2-propyl)aminocarbonyl-3(2-acetoxypropionyl) amino-2,4,6-triiodo-benzoyl chloride was reacted with 1.6 g 1,5-diamino-3-oxapentane (0.0154 mole) in 150 ml dimethylacetamide in the presence of 6.1 g tributylamine, and the reaction mixture was worked up as described in more detail in Example 1. 16.6 g 1,5-Bis-[5-(1,3-dihydroxy-2-methyl-2-propyl) aminocarbonyl-3-(2-hydroxypropionyl)amino-2,4,6-triiodo-benzoylamino]-3-oxapentane was recovered (34% yield) and melted at 225°-230° C. It gave an $R_f$ value of 0.32 with the solvent system of Example 1. Solutions containing more than 100 g of the compound per 100 ml at 20° C. were readily prepared.

EXAMPLE 12

60 g (0.1 Mole) 5-amino-2,4,6-triiodo-isophthalyl dichloride (see German Pat. No. 2,547,789) was reacted with an excess of acetoxyacetyl chloride in 240 ml dimethylacetamide. The reaction mixture was stirred into water, whereby 5-acetoxyacetylamino-2,4,6-triiodoisophthalyl dichloride having a melting point of about 240° C. was formed. The compound was reacted with two equivalent weights of 1,3-dihydroxyisopropylamine, and the reaction mixture was worked up in the manner of Example 1. 5-(1,3-Dihydroxy-isopropyl-)aminocarbonyl-3-acetoxy-acetylamino-2,4,6-triiodobenzoyl chloride melting at about 300° C. (decomp.) was recovered.

21.4 g (0.0267 Mole) of the last-mentioned compound was reacted with 2.95 g 1,4-diamino-3,6,9,12-tetraoxatetradecane (0.0125 mole) in 125 ml dimethylacetamide in the presence of 5.2 g tributylamine (0.028 mole) as described in Example 1 to produce 12.1 g 1,14-bis-[5-(1,3-dihydroxyisopropyl) aminocarbonyl-3-hydroxyacetylamino-2,4,6-triiodo-benzoylamino]-3,6,9,12-tetraoxa-tetradecane (61.3% yield) which melted at 225° C.

The compound was found to contain 27.65% C and 47.47% I (27.36% C and 48.18% I calculated for $C_{36}H_{46}I_6N_6O_{16}$) and to give an $R_f$ value of 0.16 with the solvent system of Example 1. It readily dissolved in water.

Other α, ω-bis-[5-(1,3-dihydroxyalkyl) aminocarbonyl-3-hydroxyacylamino-2,4,6-triiodo-benzoylamino]-oxoalkanes were prepared in a manner obvious from the preceding Examples and included 1,16-bis-[5-(1,3-dihydroxyisopropyl) aminocarbonyl-3-hydroxyacetylamino-2,4,6-triiodobenzoyl-amino]-4,7,10,13-tetraoxahexadecane melting at about 250° C. and 1,17-bis-[5-(1,3-dihydroxyisopropyl) aminocarbonyl-3-hydroxyacetylamino-2,4,6-triiodo-benzoyl-amino]-3,6,9,12,15-pentaoxaheptadecane melting at about 220° C.

EXAMPLE 13

An injectable contrast composition of the invention was prepared by dissoving 86 g Compound B at 37° C. in a minimal amount of bi-distilled water under a nitrogen blanket. 0.24 g Sodium bicarbonate was added to adjust the pH to 7, and the adjusted solution was passed through a filter having a pore size of 0.22/μm. The filtrate was diluted to precisely 100 ml, transferred under aseptic conditions and under a nitrogen blanket to multiple-dose vials having capacities of 10 and 20 ml, and sterilized. It contained 400 mg iodine per ml.

EXAMPLE 14

A solution of 83.7 g Compound C in a small amount of bi-distilled water was further mixed with 0.1 g sodium carbonate, 0.02 g disodium phosphate of EDTA, filtered, diluted to 100 ml, transferred to vials, and sterilized as in Example 13. This solution also contained 400 mg iodine per ml.

EXAMPLE 15

80 g Compound B, 25.6 g Compound C, 0.1 g sodium carbonate, and 0.02 g disodium phosphate of EDTA were dissolved in enough bi-distilled water in the manner of Example 14 to produce 100 ml solution which was distributed in vials and sterilized. It contained 475 mg iodine per ml.

What is claimed is:

1. An α, ω-bis-[5-(dihydroxyalkyl) aminocarbonyl-3-hydroxyacylamino-2,4,6-triiodo-benzoylamino]-oxaalkane compound of the formula

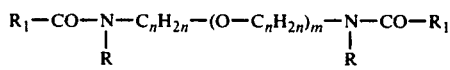

wherein
R₁ is

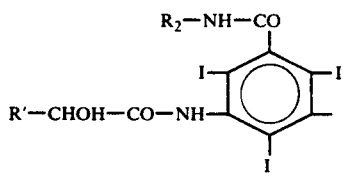

R and R' are hydrogen or methyl,
R₂ is dihydroxyalkyl having 3 or 4 carbon atoms,
n is 2 or 3,
m is an integer between 1 and 5, and
n(m+1) is an integer between 4 and 12.

2. A compound as set forth in claim 1, wherein R' is methyl, and R₂ is 1,3-dihydroxyisopropyl or 1,3-dihydroxy-2-methyl-2-propyl.

3. A compound as set forth in claim 1 which is 1,11-bis-[5-(1,3-dihydroxyisopropyl) aminocarbonyl-3-(2-hydroxy-propionyl) amino-2,4,6-triiodo-benzoylamino]-3,6,9-trioxaundecane.

4. A compound as set forth in claim 1, which is 1,14-bis-[5-(1,3-dihydroxyisopropyl) aminocarbonyl-3-(2-hydroxypropionyl) amino-2,4,6-triiodo-benzoylamino]-3,6,9,12-tetraoxatetradecane.

5. A compound as set forth in claim 1, which is 1,16-bis-[5-(1,3-dihydroxyisopropyl) aminocarbonyl-3-(2-hydroxypropionyl) amino-2,4,6-triiodo-benzoylamino]-4,7,10,13-tetraoxahexadecane.

6. A compound as set forth in claim 1, which is 1,11-bis-[N-methyl-N-{5-(1,3-dihydroxyisopropyl) aminocarbonyl-3-(2-hydroxypropionyl) amino-2,4,6-triiodo-benzoyl}-amino]-3,6,9-trioxaundecane.

7. A compound as set forth in claim 1, which is 1,16-bis-[N-methyl-N{5-(1,3-dihydroxyisopropyl)aminocarbonyl-3-(2-hydroxypropionylamino-2,4,6-triiodo-benzoyl}amino]-4,7,10,13-tetraoxahexadecane.

8. A compound as set forth in claim 1, which is 1,5-bis-[5-(1,3-dihydroxy-2-methyl-2-propyl) aminocarbonyl-3-(2-hydroxypropionyl) amino-2,4,6-triiodo-benzoylamino]-3-oxapentane.

9. A compound as set forth in claim 1, which is 1,14-bis-[5-(1,3-dihydroxy-2-methyl-2-propyl) aminocarbonyl-3-(2-hydroxypropionyl) amino-2,4,6-triiodo-benzoylamino]-4,6,9,12-tetraoxatetradecane.

10. A contrast composition opaque to X-rays consisting essentially of a physiologically tolerated aqueous carrier liquid and an effective amount of a compound as set forth in claim 1 dissolved in said carrier liquid.

11. A contrast composition opaque to X-rays consisting essentially of an aqueous carrier liquid and an effective amount of a compound as set forth in claim 2 dissolved in said carrier liquid.

* * * * *